United States Patent [19]
Kvalo

[11] Patent Number: 4,863,432
[45] Date of Patent: Sep. 5, 1989

[54] WINGED CATHETER ASSEMBLY

[75] Inventor: Michael L. Kvalo, Safety Harbor, Fla.

[73] Assignee: Critikon, Inc., Tampa, Fla.

[21] Appl. No.: 220,405

[22] Filed: Jun. 30, 1988

Related U.S. Application Data

[63] Continuation of Ser. No. 905,597, Sep. 10, 1986, abandoned.

[51] Int. Cl.⁴ ............................................. A61M 5/32
[52] U.S. Cl. ..................................... 604/177; 604/164
[58] Field of Search ................................ 604/164–170, 604/177, 283

[56] References Cited

U.S. PATENT DOCUMENTS

| | | | |
|---|---|---|---|
| 3,589,361 | 6/1971 | Loper | 604/177 |
| 4,137,916 | 2/1979 | Killman et al. | 604/170 |
| 4,324,236 | 4/1982 | Gordon et al. | 604/177 |
| 4,445,893 | 5/1984 | Bodicky | 604/177 |
| 4,563,177 | 1/1986 | Kamen | 604/177 |
| 4,565,544 | 1/1986 | Müller et al. | 604/164 |
| 4,611,382 | 9/1986 | Clark | 604/177 |
| 4,650,473 | 3/1987 | Bartholomew et al. | 604/177 |

*Primary Examiner*—C. Fred Rosenbaum
*Assistant Examiner*—Mark F. Colosimo

[57] ABSTRACT

A catheter assembly is provided to facilitate taping of the emplaced catheter onto the patient's body. The assembly comprises a catheter extending distally from a catheter hub. The hub has a hub axis co-axially aligned with the catheter and provided with a pair of opposed wings integral with the hub. Each of the wings having a proximal edge and a distal edge are such that a portion of at least one of these edges forms an acute angle with the axis of the hub of from about 35° to about 55° whereby the taping operation of the wings to the patient's body may be facilitated.

6 Claims, 5 Drawing Sheets

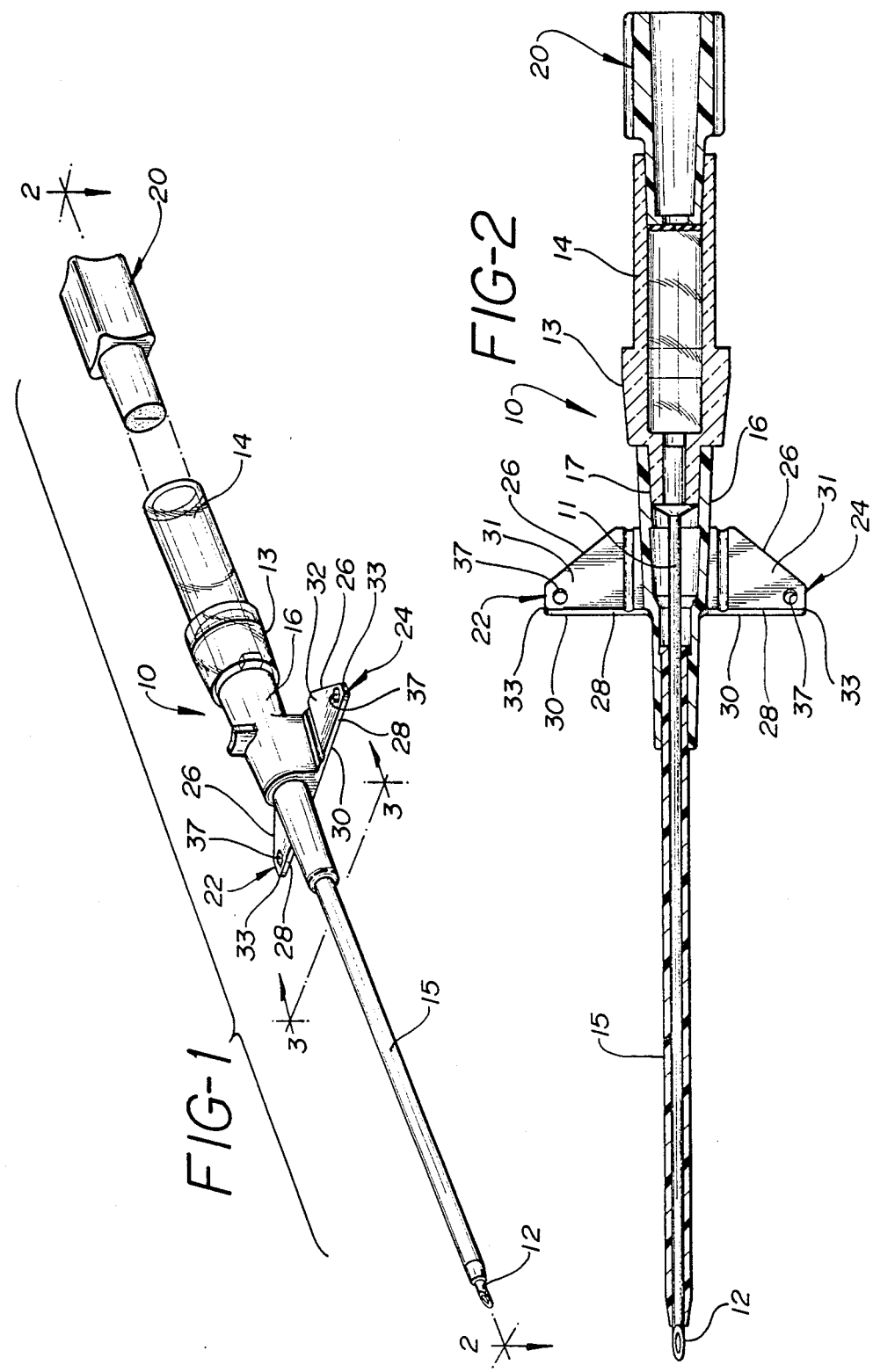

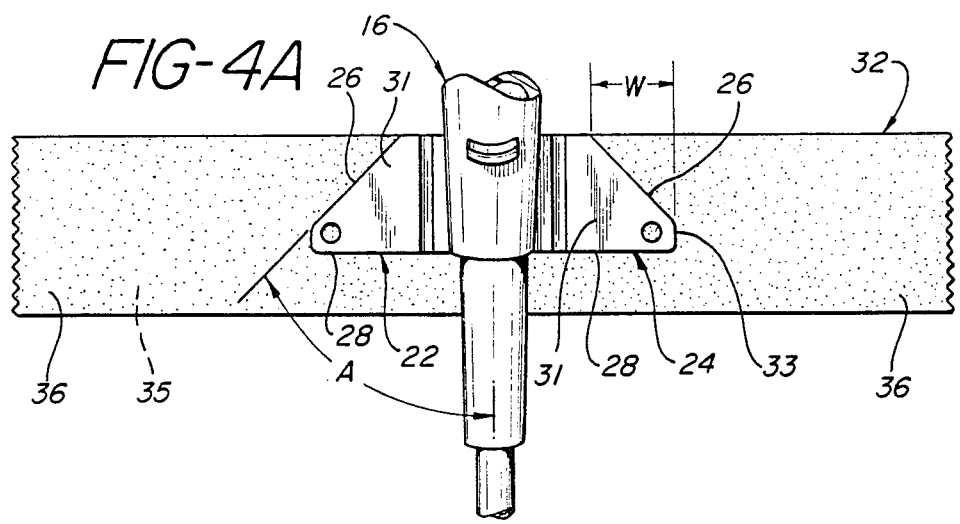
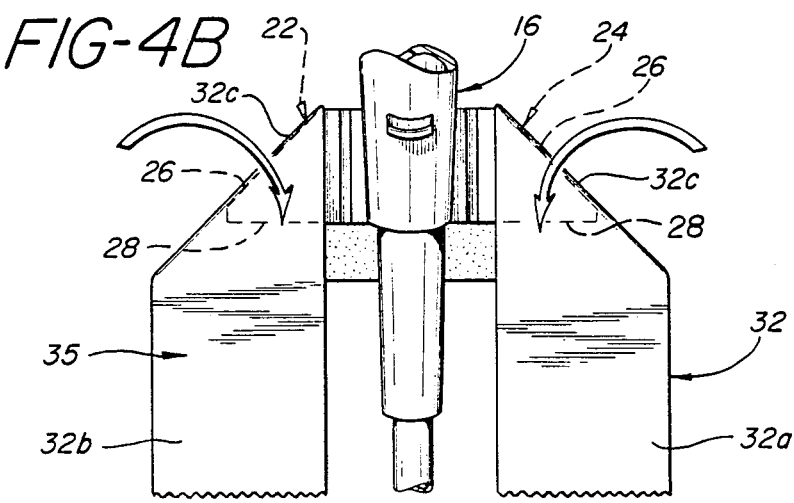
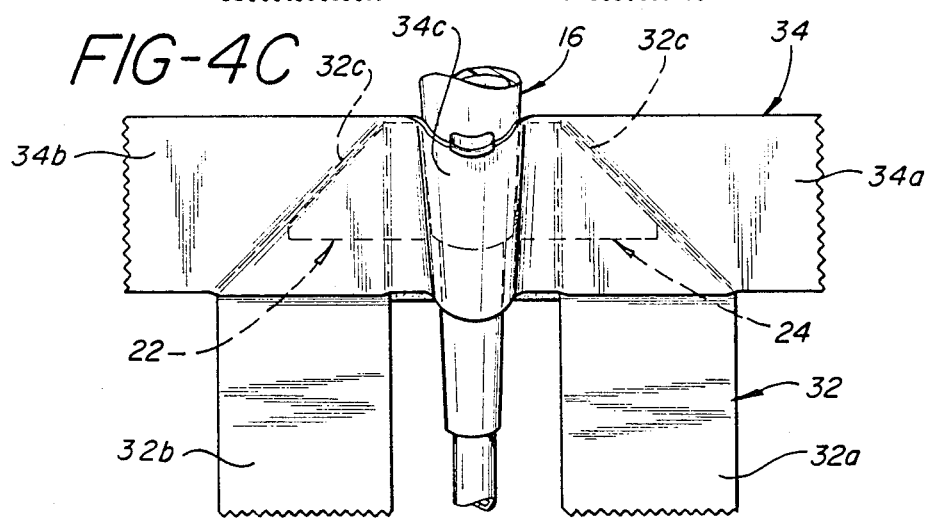

WINGED CATHETER ASSEMBLY

This is a continuation of application Ser. No. 905,597, filed Sept. 10, 1986, now abandoned.

BACKGROUND OF THE INVENTION

This invention relates, in general, to catheter assemblies and, more particularly, to catheter assemblies provided with means for anchoring the same to a patient, after the catheter has been emplaced, to prevent unwanted movement. Most specifically, this invention relates to the so-called winged catheters.

Catheter assemblies are exemplified by the over-the-needle inter vascular catheter assembly which is provided to insert a hollow catheter into a blood vessel as a means whereby fluids may be introduced into the blood stream of a patient. In such assemblies, a catheter extends distally and coaxially from a catheter hub, the hub having a lumen aligned with that of the catheter. A needle is provided, extending through the catheter hub, and through the lumen of the catheter, with a sharpened end of said needle projecting distally from the distal end of the catheter. In use, the needle is employed to pierce the skin and enter the blood vessel of the patient. The catheter is urged distally into the blood vessel and the needle is then urged proximally out of the assembly. With the needle removed, means for providing the fluid to be introduced into the blood vessel is affixed to the catheter hub so as to be in flow communication with the catheter lumen, whereafter the infusion of such fluid can begin.

It is important that at some point in this process, the catheter hub be firmly secured to the patient in that the infusion process is frequently carried out for long periods of time and there is the danger of dislodging the catheter from the blood vessel unless movement of the catheter hub relative to the patient is inhibited. While is some instances this securement is accomplished by very positive means such as suturing, most frequently pressure sensitive adhesive tape is employed. Generally, the catheter is first emplaced and then taped to the patient's body by applying a strip or strips of adhesive tape across the hub.

It has been suggested that the taping and securement of the catheter hub to the body of the patient can be facilitated if extended surfaces or wings are provided, extending from the catheter hub transversely to the direction of the axis of the hub. Adhesive tape may then be applied to these wing-like surfaces. Additionally, these wings prevent axial rotation of the hub and catheter after emplacement. Examples of such winged catheters suggestions may be found in U.S. Pat. No. 3,064,648 to A. F. Bujan; 3,352,306 to S. Hirsch; 3,589,361 to D. A. Loper et al.; 3,714,945 to V. F. Stanley; 3,769,975 to M. Nimoy et al.; 4,192,304 to M. J. Millet; 4,192,305 to C. H. Seberg; 4,193,399 to T. P. Robinsin; 4,194,504 to J. L. Harms et al.; 4,300,553 to C. H. Seberg; 4,389,210 to J. W. Genese; 4,392,856 to J. Lichtenstein; 4,366,817 to J. J. Thomas; and Des 257,885 to L. K. Kulle; as well as published U. K. Patent Application GB 2088215 to H. G. Wallace, Ltd.

In each of the above set out prior suggestions, a winged catheter is disclosed which wings may be used as surfaces for taping the hub and catheter to a patient. Typical of such securement is the method shown in the above mentioned U.S. Pat. No. 4,366,817. Here a catheter is provided with wings extending from the catheter hub. Each wing has a proximal edge and a transverse edge essentially parallel to each other and essentially perpendicular to the axis of the catheter assembly. Two strips of pressure sensitive adhesive tape are employed to secure this assembly to the patient, such strips being applied to extend, on either side of the catheter assembly, parallel to the axis of the catheter and overlying the portions of the wings remote from the catheter hub. This configuration of adhesive tape i.e., parallel to the catheter provides excellent securement for the assembly once it is so applied. Unfortunately, in actual hospital practice, this application is quite difficult to accomplish. It must be recognized that, firstly, one hand of the nurse or doctor is occupied with holding the assembly in place while with the other hand, the nurse attempts to apply the pressure sensitive adhesive tape, smoothly and securely, to the patient's arm. It will be appreciated that the adhesive tape has the unfortunate property of folding over on itself and hence is not easily applied with one hand. Further, once applied, adjustment of the tape is only possible at the expense of patient discomfort.

In view of the above, there is a need for a catheter assembly and technique for securing same to a patient in a more convenient manner than prior art suggestions.

SUMMARY OF THE INVENTION

In accordance with the teachings of this invention, a catheter assembly is provided which, in conjunction with a specific method of applying adhesive tape, may be anchored to a patient after catheter insertion without encountering the drawbacks of prior art assemblies. Specifically, the catheter assembly of this invention allows the nurse to hold the catheter assembly with one hand and to nearly and efficiently apply anchoring adhesive tape with the other hand.

The catheter assembly to which this invention applies comprises a catheter extending distally from a catheter hub. The hub has a hub axis generally coaxially alligned with the catheter and is provided with a pair of opposed wings, integral with the hub. Each of the wings extends from the hub transversely with respect to the hub axis. In accordance with the teachings of this invention, the wings, having a proximal edge and a distal edge, are such that a portion of at least one of these edges forms an acute angle with the axis of the hub of from about 35° to about 55°. It has been discovered that, with the wing edges provided within this narrowly defined angular range, the method of taping described herein may be employed by a nurse without untoward difficulty. Specifically, the method to be employed with the catheter assembly of this invention is as follows.

Firstly, prior to commencing the emplacement of the catheter assembly, the nurse first applies a strip of one-sided pressure sensitive adhesive tape with the adhesive side against that surface of the wings intended to be placed against the patient's body. The strip is applied essentially perpendicularly to the axis of the catheter and is of sufficient length to extend beyond the remote ends of each of the wings. The catheter is then inserted using normal insertion procedures. Because the non adhesive side of the tape is against the body, the tape does not interfere with the necessary movement of the catheter assembly relative to the body while the catheter is being emplaced. Having now emplaced the catheter, the nurse may place one hand on the hub to hold the assembly firmly against the patient. With the other hand the nurse may grip one extended end of the tape and fold the tape over the angular edge of the wing so that the adhesive side now faces the patient. Because of the critically narrow range of angularity chosen for the angular edge, the tape will now extend approximately parallel to the catheter axis. The nurse need only press the tape firmly into contact with the patient and repeat the procedure with the other end of the tape.

The catheter assembly is now firmly anchored to the patient so that the nurse may release the catheter hub. Preferably to insure securement, a second strip of adhesive tape is applied, adhesive side toward the patient, overlying the hub and wings and extending transversely to the axis of the catheter, on either side of the wings. The extended portion of this second strip is adhered to the patient. Accordingly, the catheter assembly is secured in both the transverse an the axial directions.

BRIEF DESCRIPTION OF THE DRAWINGS

FIG. 1 illustrates, in perspective view, a preferred embodiment of the catheter assembly of this invention;

FIG. 2 is a cross-sectional planar view of the catheter assembly of FIG. 1 taken along lines 2—2;

FIG. 4A is a partial planar view of the catheter assembly of FIG. 1, after a first step i the process of applying the anchoring adhesive tape;

FIG. 4B is a partial planar view of the catheter assembly of FIG. 1, after a further step in the process of applying the anchoring tape;

FIG. 4C is a partial planar view of the final step in the process of applying the anchoring tape;

DETAILED DESCRIPTION OF THE INVENTION

Figure 3:
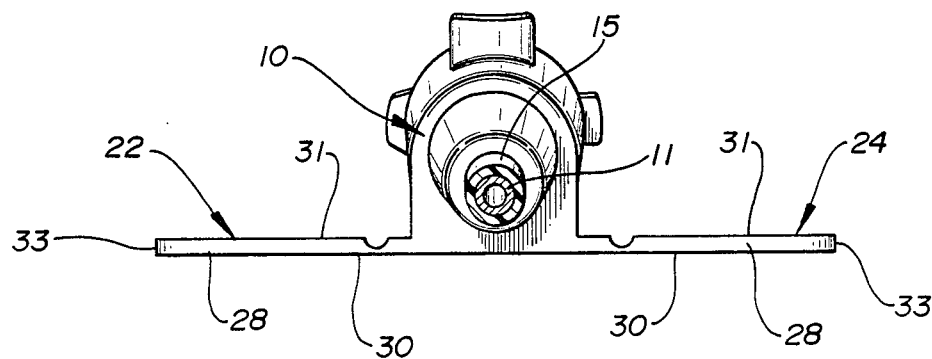
FIG. 3 is a transverse cross-section view of the catheter assembly of FIG. 1 taken along line 3—3.

Referring to FIGS. 1-3, illustrated therein is a preferred embodiment of the catheter assembly 10 of this invention. The assembly comprises an introducer needle 11 which is in the form of a hollow hypodermic needle having a point 12 on one end thereof. Needle 11 is secured at its blunt end to a needle hub 13 which has a transparent blood detecting chamber 14 integral with its proximal end. The entire hub and blood detecting chamber assembly may preferably be molded in one piece from a suitably clear plastic material e.g. polypropylene, polyacrylate, polycarbonate, or styrene butadiene copolymer. Needle 11 serves the function of introducing a flexible polymeric catheter 15 into a blood vessel. Catheter 15 is attached to a catheter hub 16 at its proximal end and hub 16 is adapted to be removably secured to a fitting 17 on the distal end of needle hub 13. A plug 20 is provided for insertion into the proximal end of blood detecting chamber 14 to close such chamber against the passage of blood therefrom.

To emplace the catheter 15, the assembly a shown in FIG. 1, with the needle 11 and plug 20 in place, is employed. The needle 11, with its protruding end 12, is used to pierce the skin and blood vessel of the patient. Thereafter the catheter 15 is urged distally to be seated in the blood vessel and the needle is urged proximally to be removed from the assembly together with the needle hub 13 and plug 20. A fluid administration means may now be placed in flow communication with the catheter hub 16 and the catheter 15.

As described above, at some point in this process, it is necessary to secure the catheter and catheter hub to the patient, preferably by the use of adhesive tape. To this end the assembly 10 has been provided with wings 22 and 24, extending from the catheter hub 16 in a direction transverse to the longitudinal axis of the coaxial catheter hub and catheter. Each of said wings 22 and 24 comprise proximal edges 26, distal edges 28, a body facing surface 30, a top surface 31 and extreme ends 33. The wings 22 and 24 provide a convenient surface for applying the adhesive tape and may also be used for anchoring the assembly by suturing, employing suture holes 37.

Additionally, the wings 22 and 24 are each provided with hinges or notched areas 25, to facilitate the planar wings conformance with the surface of the patient. In accordance with the teachings of this invention, a portion of one edge e.g., the proximal edge 26 in the embodiment shown in FIGS. 1-3, is angular, forming an acute angle with the longitudinal axis of the coaxial catheter-catheter hub assembly. The acute angle, angle A in FIG. 4A, may range from about 35° to about 55° and, preferably, from about 40° to 50° e.g., 45°. The portion of the angular edge which is at the above prescribed angle should be sufficient so that the transverse projected length of this portion, dimension W in FIG. 4A, is approximately at least as long as a substantial fraction of the width of the strip of adhesive tape being employed, e.g. about at least one third of the width of such adhesive tape. Preferably, this transverse projected length W should range from about 0.125 to about 0.75 inches and still more preferably from about 0.15 to about 0.25 inches e.g., 0.19 inches.

The importance of the above prescribed geometric relationships will become apparent from consideration of FIGS. 4 and 4a-c, wherein the taped catheter assembly as well as the taping steps are illustrated.

Figure 4:
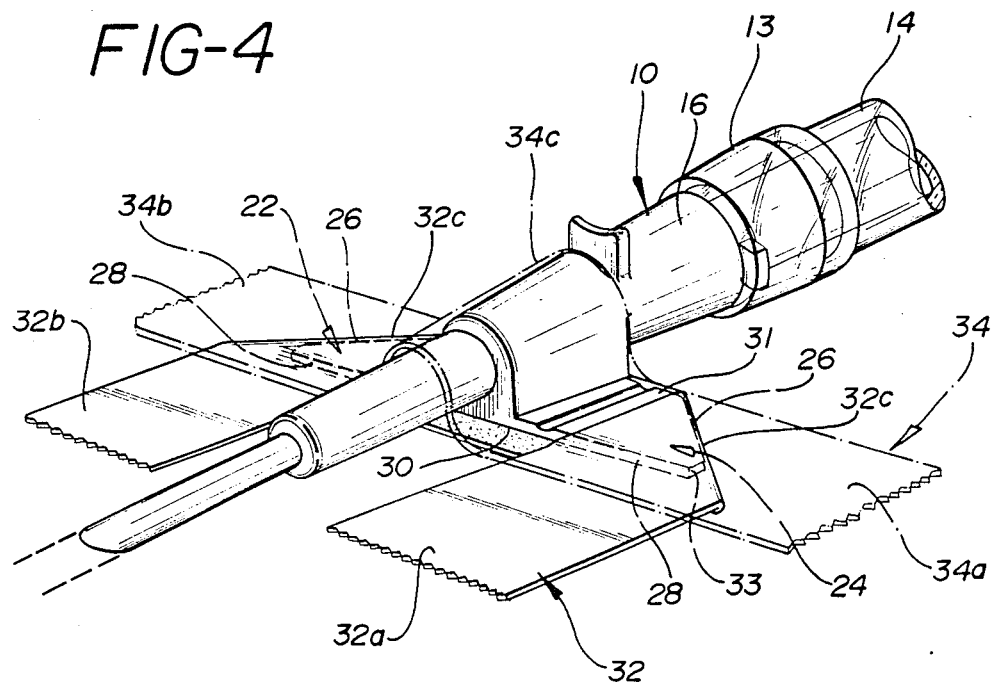
FIG. 4 illustrates, in perspective view, the preferred embodiment of the catheter assembly of this invention anchored to a patient's body with adhesive tape.

FIG. 4 illustrates the catheter assembly of this invention securely taped to the body of a patient (not shown). A first strip of adhesive tape 32 is adhered to the patient's body with the first tape strip legs 32a and 32b extending essentially parallel to the axis of the catheter and with the central portion 32c adhered to the body facing surface of the catheter hub 16 and wings 22 and 24. A second strip of adhesive 34 is applied with the central portion thereof 34c being adhered to the top of the hub 16 and the top surface of the wings 22 and 24 and the second tape strip legs 34a and 34b extending beyond the ends of the wings and being adhered to the patient FIGS. 4A-C illustrates the steps employed in achieving the secured configurations shown in FIG. 4. Referring to FIG. 4, prior to inserting the catheter into the patient, the user first applies first tape strip 32 to the catheter with the central portion of the tape 34c being adhered to the bottom or body side of the catheter hub and the body side surface of the wings. The first tape strip legs 32a and 32b then extend beyond the ends of the wings with their adhesive coated surfaces 36 facing upwardly. Accordingly, the catheter may be inserted into the patients blood vessel and the applied first adhesive tape strip 32 will not interfere as it is the non-adhesive coated surface 35 that contacts the patient.

After insertion (referring to FIG. 4B) the nurse, holding the catheter assembly in place with one hand, may now simply grip the remote ends 36 of each of legs 32b and 32a, and fold these portions of tape strip 32 over the wings 22 and 24 and parallel to the axis of the catheter-catheter hub. It can be seen that by providing an angular portion for proximal edge 26, within the narrow range of about 35°–55°, legs 32a and b will be approximately parallel to the axis of the assembly and fold neatly over the wings. This is facilitated by having the projected length of the angular portion W in FIG. 4A, dimensioned to a length essentially at least that of the width of the tape strip 32.

Referring to FIG. 4C, having now secured the catheter assembly to the patient, the nurse may now release the same and, for added securement, apply a second adhesive tape strip 34. This adhesive strip may be applied, adhesive side down, with its central portion 34c overlying the catheter hub and adjacent wing surfaces and with legs 34a and 34b, extending beyond the wings onto the patient's body.

The embodiment illustrated in FIGS. 1–4, and 4A–C comprises certain preferred features of this invention. For example the angular edge is chose to be the proximal edge 26 of the wings so that the tape legs 32a and 32b will extend toward the catheter and away from potentially encumbering apparatus such as the liquid administration set or other devices to be employed in conjunction with the catheter. Further, the angular portion is on the part of the wings most remote from the catheter hub giving the nurse maximum access to maneuver the tape. Nevertheless, in certain circumstances other variations of this invention may be more appropriate. Some of these possible variations are briefly described below in consideration together with FIGS. 5–7.

Figure 5:
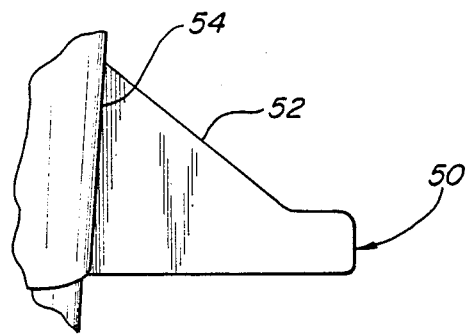
FIG. 5 is a second embodiment of the catheter assembly of this invention shown in a view similar to that of FIG. 4b.

In FIG. 5 there is illustrated in planar view, a portion of an alternative shape for a wing 50 incorporating the teachings of this invention. As can be seen from this Figure, the angular portion of proximal edge 52 is adjacent to catheter hub 54 rather than remote therefrom. Accordingly, the adhesive tape to be applied will be closer to the hub and catheter when the legs thereof extend parallel to the patient. It should be understood that the angular portion may also encompass the entire length of the proximal edge of a wing.

Figure 6:
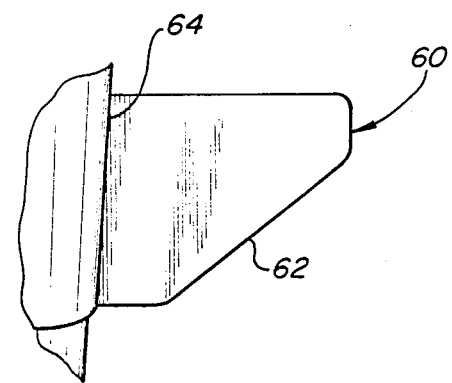
FIG. 6 is a third embodiment of the catheter assembly of this invention shown in a view similar to that of FIG. 4b.

In FIG. 6, there is illustrated in planar view a portion of another alternative shape for a wing 60, incorporating the teachings of this invention. As can be seen from this figure, the angular portion of the edge is a portion of distal edge 62 and on the portion remote from catheter hub 64. Accordingly, the adhesive tape to be applied will extend proximally from the catheter hub instead of distally as in the prior embodiments.

Figure 7:
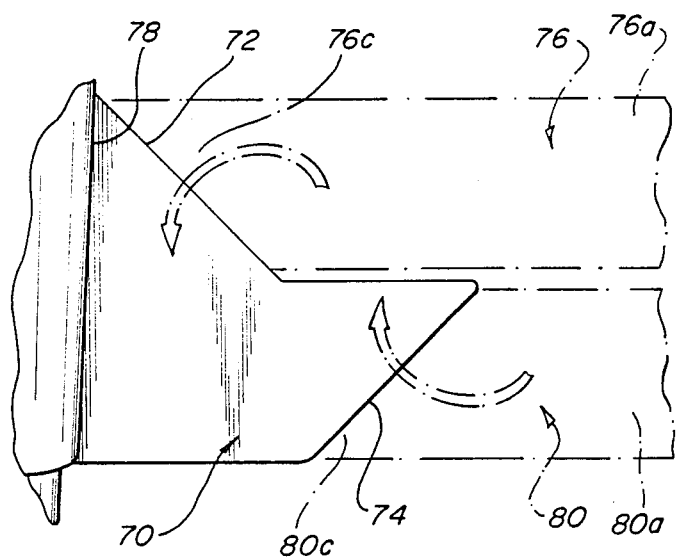
FIG. 7 is a fourth embodiment of the catheter assembly shown in a view similar to that of FIG. 4b.

The wing shape illustrated in FIG. 7, provides still another embodiment wherein both the adjacent portion of the proximal edge 72 of wing 70 and the remote portion of distal edge 74 are angular. This embodiment allows for an advantageous method of applying two strips of adhesive tape to the patient with use of only one hand. Specifically, prior to emplacing the catheter assembly, the nurse applies a first strip 76 with the adhesive side of the central portion of the strip 76c adhered to the proximal portion of the bottom (patient facing side) of the catheter hub 78 and the wings 70 and with the leg portions of strip 76 (leg 76a being illustrated in FIG. 7) extending beyond the wings. Similarly, a second strip 80 is applied with the adhesive side of the central portion of the strip 80c adhered to the distal portion of the bottom (patient facing side) of the catheter hub 78 and the wings 70 and with the leg portions of strip 80 (leg 80a being illustrated in FIG. 7) extending beyond the wings.

The catheter assembly shown in FIG. 7 is emplaced, and again, because the adhesive surfaces of strip 76 and 80 are face up, the tape does not interfere with placement. Once emplaced the nurse may now hold the catheter against the patient with one hand and with the other grip a first remote end of strip 76 and fold the strip over proximal edge 72, parallel to the axis of the catheter and in the distal direction. Next, without releasing the catheter assembly, the nurse may grip the second remote end of strip 76 and also fold the strip over the proximal edge 72 parallelly and in the distal direction. Then, again without releasing the catheter, the nurse may grip a first remote end of strip 80 and fold the strip over the distal edge 74 of the wing, parallel to the axis of the catheter and, this time, extending in a proximal direction. Finally, still without releasing the catheter, the nurse may fold the second remote end of tape 80 in a similar fashion.

Figure 8:
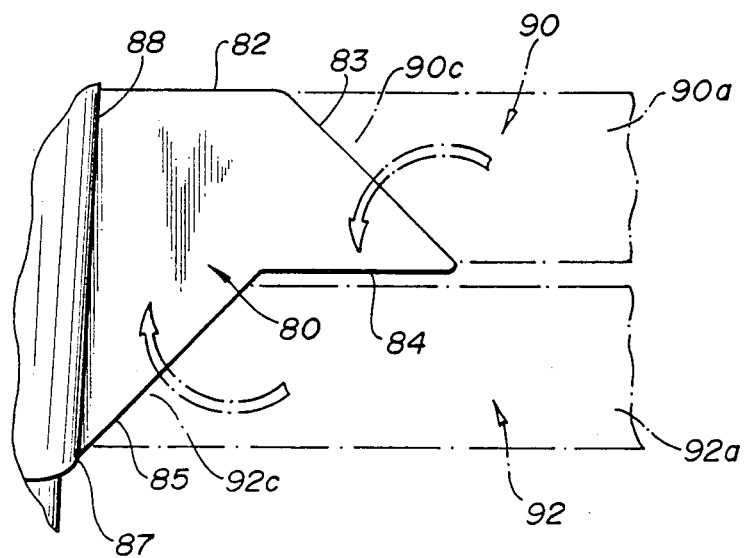
FIG. 8 shows a further embodiment of the catheter assembly shown in a view similar to that of FIG. 4B.

The wing shape illustrated in FIG. 8 provides still another embodiment showing catheter hub 88 with wing 80 projecting transversely from one side of hub 88. A similar sing (not shown) projects transversely from the other side of catheter hub 88. The proximal edge 82 of wing 80 includes a tape folding edge portion 83 which forms an acute angle with the axis of hub 88. Tape forming edge 83 intersects proximal edge 82 of wing 80 at a point spaced transversely apart from catheter hub 88 along proximal edge 82. The distal edge 84 of wing 80 includes a straight tape forming edge 84 which forms an acute angle with the axis of hub 88 and it intersects distal edge 84 of wing 80 at a point 87 adjacent hub 88.

Like the embodiments of FIG. 7 above, the embodiment of FIG. 8 allows the user to apply two strips of adhesive tape to the patient while using only one hand. Prior to emplacing the catheter assembly, the nurse applies a first adhesive strip 90 with the adhesive side of the central portion of the strip 90C adhered to the proximal portion of the bottom (patient facing side) of catheter hub 88 and the wing 80 and with the leg portion 90A of strip 90 extending beyond wing 80. Similarly, a second strip 92 is applied with the adhesive side of the central portion of the strip 92C adhered to the distal portion of the bottom (patient facing side) of catheter hub 88 and wing 80 and with the leg portions 92A of strip 92 extending beyond wing 80.

The catheter assembly shown in FIG. 8 is emplaced, and again, because the adhesive surfaces of strips 90 and 92 are face up, the tape does not interfer with placement. Once emplaced, the nurse may now hold the catheter against the patient with one hand and with the other hand grip leg portion 90A of strip 90 and fold it over proximal tap folding edge 83 parallel to the axis of catheter 88 and in the distal direction. Next, without releasing the catheter assembly, the nurse may grip the leg portion 92A of second strip 92 and also fold strip 92 over the distal tape folding edge 85 parallel to the axis of the catheter and in the proximal direction. Wing 80 is now taped down to the patient. The nurse does the same thing with the wing (not shown) on the other side of catheter hub 88.

I claim:

1. In a catheter placement assembly comprising a catheter extending distally from a catheter hub, said hub having a hub axis generally co-axially aligned with said catheter and having a pair of opposed wings, integral with the hub and each extending from the hub in a direction transverse to the hub axis each of said wings having a bottom surface adapted to abut the patient and an opposed top surface each of said wings having a proximal facing edge and a distal facing edge, said wings adapted to receive at least one strip of tape to hold said catheter hub on the patient; the improvement wherein each of said proximal facing edges of said wings includes a straight tape forming edge portion (i) extending outward from said hub and (ii) angled toward said distal facing edge at an acute angle with the axis of said hub of from about 35 to about 55 degrees; the method of attaching said catheter placement assembly to a patient comprising:

affixing a piece of attachment tape along said bottom surface of said wings generally transversely to said catheter hub axis such that a portion of the tape will extend beyond said tape forming edge portion; and folding said tape over said tape forming edge portion; and attaching the tape to the patient in a direction extending generally parallel to said hub axis so as to provide a retention force directed toward said distal end of said catheter.

2. In the catheter placement assembly of claim 1 wherein said tape forming edge portion forms an acute angle with the axis of the hub of from about 40 to about 50 degrees.

3. In the catheter placement assembly of claim 1 wherein the length of said tape forming edge portion is at least as long as a substantial fraction of the width of the strip of adhesive tape to be employed.

4. In the catheter placement assembly of claim 2 wherein said substantial fraction is at least one third.

5. In the catheter placement assembly of claim 1 wherein the length of said tape forming edge portion is at least about 0.125 inches long.

6. In the catheter placement assembly of claim 1 wherein each of said wings includes a second tape forming edge portion on said distal facing edge of said wings which tapers outwardly from said hub and toward said proximal facing edge of each of said wings.

* * * * *